(12) United States Patent
Simon et al.

(10) Patent No.: US 6,652,868 B1
(45) Date of Patent: Nov. 25, 2003

(54) METHOD OF PEELING AND PRODUCTION OF A PREPARATION FOR ITS IMPLEMENTATION

(76) Inventors: Veronique Simon, 40, avenue du President Wilson, F-75016 Paris (FR); Michel Dubourdeaux, 32, boulevard Andre Bost, F-63270 Vic-le-Comte (FR); Daniel Jean, 283, rue de la Chaussade, F-63270 Vic-le-Comte (FR)

( * ) Notice: Subject to any disclaimer, the term of this patent is extended or adjusted under 35 U.S.C. 154(b) by 0 days.

(21) Appl. No.: 09/856,503

(22) PCT Filed: Dec. 16, 1999

(86) PCT No.: PCT/FR99/03161

§ 371 (c)(1), (2), (4) Date: Jul. 30, 2001

(87) PCT Pub. No.: WO00/35406

PCT Pub. Date: Jun. 22, 2000

(30) Foreign Application Priority Data

Dec. 17, 1998 (FR) .............................................. 98 15944

(51) Int. Cl.⁷ ............................ A61K 7/00; A61K 35/78
(52) U.S. Cl. ...................... 424/401; 424/725; 424/765; 424/777
(58) Field of Search ............................... 424/401, 195.1, 424/489, 494, 602; 514/574

(56) References Cited

U.S. PATENT DOCUMENTS

| | | | | |
|---|---|---|---|---|
| 5,578,312 A | * | 11/1996 | Parrinello | |
| 5,639,459 A | * | 6/1997 | Bouras | 424/195.1 |
| 5,730,991 A | * | 3/1998 | Rapaport | 424/401 |
| 5,922,359 A | * | 7/1999 | Youssefyeh | 424/570 |
| 6,024,960 A | * | 2/2000 | Kharazmi et al. | 424/195.1 |
| 6,133,317 A | * | 10/2000 | Hart | 514/574 |

* cited by examiner

*Primary Examiner*—Russell Travers
*Assistant Examiner*—Gina Yu
(74) *Attorney, Agent, or Firm*—Shoemaker and Mattare

(57) ABSTRACT

A method of superficial epidermal peeling in a human comprising massaging unto the horny layer of the epidermis (stratum corneum), a composition comprising vegetable-derived elements characterized by sufficient length and rigidity to enter into the horny layer, improving the constitution of the skin tint, smoothing the skin surface, removing wrinkles, blemishes, localized hyperkeratoses and reducing skin pore size by regulating seborrhea.

6 Claims, No Drawings

METHOD OF PEELING AND PRODUCTION OF A PREPARATION FOR ITS IMPLEMENTATION

This application is a 371 case of PCT/FR99/03161 which claims the priority date of Dec. 16, 1999.

This invention relates to a method of peeling as well as to the production of a preparation for its implementation.

In dermo-cosmetological practice, "peeling" conventionally refers to a treatment that consists in causing, by means of chemical products, a destruction of cellular layers that form the epidermis, over a variable depth based on the intensity of the peeling, in order to induce an exfoliation of these layers, then their regeneration, i.e., their replacement by new cellular layers.

The peeling thus makes it possible to eliminate a certain number of imperfections that are present on the surface of the skin such as open pores, blemishes, seborrheic warts, wrinkles, localized hyperkeratoses, superficial scars, etc.

To date, various chemical products have been proposed, which all have in common acting by a powerful keratolytic effect. Among those that are most frequently used, it is possible to cite phenol, resorcinol, trichloroacetic acid, glycolic acid and the other alpha-hydroxylated acids.

The progression of these products within cellular layers of the epidermis and, consequently, their depth of action are sometimes difficult to monitor. Reaching the basal layer of the epidermis, however, and even the underlying dermis, can have extremely negative consequences. Thus, brown spots can appear secondarily in the case of lesion of the basal epidermal layer, while a definitive depigmentation of the skin can develop in the event of the dermis and pilosebaceous passages being reached. Finally, intoxication cases have been reported, in particular with the use of phenol, due to a systemic penetration of the latter.

As a result, peeling as it is practiced to date, if it constitutes a very effective technique for improving the appearance of the skin, exhibits non-negligible risks that justify in particular the fact that it can be used only by professionals in the field of dermo-cosmetology.

Another technique for improving the appearance of the skin, which is also widely used in dermo-cosmetology, consists in eliminating a more or less large portion of the surface layers of the epidermis by an abrasion, i.e., a purely mechanical action.

First of all, there are so-called scrubbing or exfoliating products, also called "scrubs" in English terminology, that come in the form of creams or gels and that contain particles that, when they are used to massage the skin, are able to cause an exfoliation of dead epidermis cells—i.e. the horny layer—by an abrasive action. These scrubbing products, which are described in particular in Japanese Patent Applications Nos. 3-106809 and 6-072827, European Patent Application No. 692 236, International Application PCT No. 94/12151, and the article of NAKAHIRA et al. published in COSMETICS & TOILETRIES (1986, 101, 41–47) are primarily intended for wide-spread public use. They are thus designed to exhibit, under normal conditions of use, only a very superficial exfoliating action, limited to several cellular layers of the horny layer, which makes possible an in-depth cleaning of the skin, but which is unsuitable for eliminating or even reducing the imperfections that the latter may comprise.

Furthermore, the professionals of dermo-cosmetology use a so-called "dermabrasion" technique whose purpose is to eliminate the entire horny layer by fine sanding of the cells of this layer with grinders.

Finally, for several years, the dermatologists have resorted to the use of laser rays that make it possible to cause destruction by burning the epidermis.

If these two latter methods, dermabrasion and laser, are sensible means, in the hands of professionals, for ensuring better monitoring of the depth of the skin destruction than the chemical peeling, it turns out, however, that their use is not totally without undesirable secondary effects such as dyschromias, retractions, weight loss and embrittlement of the skin covering. The dermabrasion, moreover, exhibits the drawback of being extremely uncomfortable for the person in whom it is carried out and cannot be used over the entire face, in particular under the eyes where the skin is too fine. With regard to laser rays, they create the risk of a resurgence of the herpes virus in subjects that have undergone a primary infection that requires taking an antiviral treatment prior to its use.

What is more, the practice of the dermabrasion or the laser should be compared to a true surgical intervention that requires a wide-area local anesthesia, and even a general anesthesia, and that indicates long and sometimes uncertain operating procedures.

The problem is posed, consequently, of using new techniques making it possible to eliminate, or, at the very least, to reduce the imperfections that can be exhibited by the surface of the skin so as to improve the appearance thereof, and that are, in a general manner, free of all of the drawbacks indicated above.

More particularly, the problem is posed of using new techniques that, while making it possible to obtain a satisfactory skin resurfacing, have a limited action in the thickness of the epidermis so as to prevent any lesion of the basal layer of the dermis or of the underlying dermis, and, consequently, the unexpected occurrence of inopportune secondary effects, and even consequences that go against the desired object.

Finally, it is desirable that these techniques be characterized by safety and simplicity of use such that their use does not necessarily impose the intervention of a professional in the field of dermo-cosmetology and is accessible to any person desiring to improve the appearance of his skin.

The inventors, however, noted that it is possible to induce, by the introduction, in the thickness of the horny layer of the epidermis, a multitude of elements of very small size, a separation and a cleavage of this horny layer in its entirety that end in its elimination and its replacement by new cellular layers, and, consequently, in a notable improvement in the appearance of the surface of the skin, and this, without risk of lesion of the basal layer of the epidermis, nor of the underlying dermis.

The inventors therefore developed, on the basis of these findings, a new method for embellishing the appearance of the skin that, although not using a chemical product with keratolytic effect, will be referred to below as "method of peeling," to the extent that it makes it possible to obtain, like the chemical peeling, an exfoliation of superficial cellular layers of the epidermis and their regeneration.

This invention therefore has as its object a peeling method that is characterized in that it comprises the introduction, in the thickness of the horny layer of the epidermis, of elements whose length is between about 5 and 100 microns and that have a tapered shape and an adequate rigidity to be able to penetrate said horny layer.

Within the meaning of this invention, "tapered shape" element means any element that has the general shape of a needle or pin, i.e., that has a length much greater than its width and whose ends end in points. Furthermore, within the scope of this invention, it is considered that an element has an adequate rigidity to be able to penetrate the horny layer when, this element being deposited on the surface of the skin, it is able, taking into account its tapered shape, to penetrate the horny layer and advance into the thickness of this layer under the effect of a simple manual massage.

According to an advantageous arrangement of this peeling method, the elements that are introduced into the thickness of the horny layer are elements of vegetable origin. Actually, a large number of elements that meet the criteria of size, shape and rigidity mentioned above and that, by their natural origin, offer a perfect safety, which makes their use particularly suitable for the implementation of the peeling method according to the invention, are found among the vegetables.

These elements of vegetable origin are preferably selected from among the fibers, the hairs and the crystals of calcium oxalate.

According to the invention, vegetable fibers of lignin and/or cellulose (pectocellulose, hemicellulose, . . . ), which come in the form of pins and have a length of about 5 to 50 microns, are preferably used. Such fibers are exhibited in numerous ligneous tissues and, in particular, in the wood of *Cercis australis, Ledum palustre* and *Myricaria germanica.*

Furthermore, as far as the hairs are concerned, it is preferred to use hairs that have a length of between about 20 and 100 microns, to the extent that they generally exhibit a rigidity that ensures optimum penetration of the horny layer. By way of examples of hairs that are particularly well-suited to the implementation of the peeling method according to the invention, it is possible to cite the hairs that are present on the surface of *Ficus carica* leaves and those that are present in the fruits of *Rosa canina, Urtica urens,* and *Urtica dioica.*

As for calcium oxalate crystals, those that come in the form of raphides, i.e., clusters of fine crystalline needles, have proven to be the most advantageous. Such crystals are present in a large number of monocotyledonous species, but also in a certain number of dicotyledonous species such as those that belong to the genera Yucca, Tamus, Diffenbachia or else Asparagus.

According to another advantageous arrangement of the peeling method according to the invention, the introduction of elements in the thickness of the horny layer is obtained by a massage of skin areas to be treated, with these elements. This massage, which can be carried out manually or by means of a suitable device, is preferably light and uniform and of a period advantageously between 1 and 10 minutes and preferably on the order of 2 to 5 minutes. It is thus possible to obtain a very satisfactory penetration of elements in the horny layer by a technique that is neither painful nor aggressive for the skin and that offers, moreover, the advantage of requiring neither a specific material nor a particular dexterity.

According to the invention, the massage of skin areas to be treated with the elements can be carried out by using the latter in different forms. Thus, for example, when the elements that are intended to be introduced into the thickness of the horny layer are hairs that are present on the surface of a vegetable element such as a leaf, the massage can be carried out by directly rubbing the skin areas to be treated with this element or a fragment of the latter.

As a variant, it is also possible to carry out this massage with a more or less developed preparation that contains the elements that are intended to be introduced into the thickness of the horny layer, such as:

a powder that is obtained, for example, by a spraying of elements (leaves, stems, fruits, . . . ) or vegetable tissues (wood, for example), known for exhibiting fibers, hairs or calcium oxalate crystals that are suitable for the implementation of the peeling method according to the invention and that come in dehydrated form, optionally followed by one or more sieving procedures that are suitable for increasing the content of the resulting powder of fibers, hairs or calcium oxalate crystals as appropriate;

a suspension that can be prepared either by a grinding of these same elements or vegetable tissues, but in a fresh or rehydrated form, optionally followed by a dilution of the ground material in a liquid phase (water, water/glycerol, oil, . . . ) and one or more sieving procedures, either by suspending a powder as obtained above in a liquid phase; or else a more complex formulation of cream, milk or gel type, prepared according to the same principles.

Regardless of the manner in which the massage is carried out, the penetration of elements in the thickness of the horny layer is reflected, in a first step, by the appearance of a slight redness, which is gradually amplified generally by accompanying a sensation of heat, and which disappears at the end of several hours. Then, about 2 to 3 days after the massage is carried out, a very uniform exfoliation, with regard to the thickness and the surface on which it is produced, is observed at the treated skin areas. This exfoliation shows, in fact, a separation and a cleavage of the horny layer as a whole relative to the underlying cellular layers of the epidermis. This separation and this cleavage result from an intake of interstitial fluids between the horny layer and these underlying epidermal layers, which is itself induced by the penetration and the progression of elements in the thickness of the horny layer. The exfoliation of the horny layer is accompanied by a renewal of this layer, starting from underlying epidermal cells, which can be maintained by carrying out a peeling according to the invention at regular intervals.

An improvement in the constitution of the tint, i.e., its lustre, a smoothing of the surface of the skin by reducing wrinkles, a considerable reduction of blemishes and localized hyperkeratoses, and, in skin with a tendency toward seborrhea, a reduction of the size of skin pores by regulation of seborrhea, are thus obtained.

According to the invention, the massage is advantageously followed by a cleaning and/or a rinsing of treated skin areas, then the application, in these areas, of a cosmetic composition that is high in fatty substances, such as, for example, oils, and in particular vegetable oils (Jojoba oil, sesame oil, hydrogenated palm oil, kernel oil, . . . ), waxes (beeswax, *Euphorbia serifera* wax, . . . ) or fatty acid esters or triglyceride esters (glycerol stearate, glyceryl stearate, polyglycerol isostearate, isostearyl neopentonate, cetyl palmitate, triglyceride esters and caprylic acid or capric acid, . . . ) so as to promote the rebuilding of the epidermis.

It is also possible to initiate, in the following days, a daily application of a cosmetic composition based on compounds that have inhibitory properties on the pigmentation of the skin, such as hydroquinone and its monomethyl ether (mequinol) or kojic acid, to preclude a possible reappearance of blemishes, in particular in subjects who have skin with a pigmentogenic tendency (black skin, cross-breed skin, Asiatic skin, . . . ).

Finally, in the cases of skin hypersensitivity, in addition, cosmetic compositions that soften, soothe or are suitable for reducing possible edema will be used.

The peeling method according to the invention offers numerous advantages. Actually, while making it possible to improve very effectively the appearance of the surface of the skin, it does not create, contrary to chemical peeling techniques, dermabrasion and laser ray burning used to date, any risk of lesion of the basal layer of the epidermis, nor of the underlying dermis, and, consequently, any of the secondary effects inherent to these techniques. Furthermore, it is neither painful nor even uncomfortable and can be applied over all of the skin areas, including the most fragile areas. Finally, by its safety and its simplicity of use, it can be used by private individuals as well as by professionals.

This invention also has as its object the use of elements whose length is between about 5 and 100 microns and that have a tapered shape and an adequate rigidity to be able to penetrate the horny layer of the epidermis, for the production of a preparation for the implementation of a peeling method as defined above.

According to an advantageous implementation of this use, the elements are elements of vegetable origin.

According to a preferred arrangement of this advantageous implementation, these elements of vegetable origin are selected from among:

the fibers, and, more particularly, from among the lignin fibers and cellulose fibers that come in the form of pins and have a length of about 5 to 50 microns;

the hairs, and, in particular, from among the hairs that have a length of between about 20 and 100 microns; and the calcium oxalate crystals, and, preferably, from among the oxalate crystals that come in the form of raphides.

In a particularly preferred manner, the elements are selected from among the fibers of the wood of *Cercis australis, Ledum palustre* and *Myricaria germanica,* the hairs of *Ficus carica* leaves, the hairs of fruits of *Rosa canina, Urtica urens* and *Urtica dioica,* and the raphides of calcium oxalate that are present in the species that belong to the genera Yucca, Tamus, Diffenbachia and Asparagus.

According to the invention, the preparation advantageously contains an amount of elements that is between 20 and 60%, and, more particularly, between 30 and 40% by weight of the total weight of said preparation, and that is preferably selected based on the ethnic group by whom it is intended to be used, so as to take into account skin specificities characteristic of each of these groups.

Also according to another advantageous arrangement of the use according to the invention, the preparation comes in the form of a cosmetic composition that contains the elements in suspension in a physiologically acceptable vehicle and that contains, for example, one or more fatty substances that are suitable for a cosmetic use such as those cited above, so as to impart to this preparation a texture that is particularly suited to use by massage.

Such a cosmetic composition, which can come in the form of a cream, a milk, a gel or a suspension, is able to be prepared by a process that comprises:

the grinding of elements or vegetable tissues that are known for having fibers, hairs or calcium oxalate crystals that are suitable for the implementation of the peeling method according to the invention, the passage of the ground material into one or more sieves that have meshes that are at most equal to 500 microns, advantageously 200 microns, and, preferably, 100 microns, so as to increase the content of this ground material of fibers, hairs or calcium oxalate crystals as appropriate, the suspending of the ground material in a physiologically acceptable vehicle and the homogenization of the resulting suspension.

As a variant, the preparation can come in the form of a simple powder that is obtained by, for example, a spraying of elements or dehydrated vegetable tissues, optionally followed by one or more sieving procedures.

This invention also has as its object a preparation for the implementation of a peeling method as defined above, whereby this preparation comprises elements whose length is between about 5 and 100 microns and is characterized in that these elements are tapered, exhibit an adequate rigidity to be able to penetrate the horny layer of the epidermis, and are selected from among the fibers of the wood of *Cercis australis, Ledum palustre,* and *Myricaria germanica,* the hairs of *Ficus carica* leaves, the hairs of fruits of *Rosa canina, Urtica urens,* and *Urtica dioica,* and the calcium oxalate raphides that are present in the species that belong to the genera Yucca, Tamus, Diffenbachia and Asparagus.

According to the invention, this preparation advantageously contains an amount of elements that is between 20 and 60% and, more particularly, between 30 and 40% by weight of the total weight of said preparation, and this is also preferably selected based on the ethnic group by whom it is intended to be used.

Furthermore, it preferably comes in the form of a cosmetic composition that comprises the elements in a physiologically acceptable vehicle.

In addition to the preceding arrangements, the invention also comprises other arrangements that will emerge from the following description and refers to examples of implementation of the peeling method according to the invention and preparations that are suitable for this implementation.

It should be understood, however, that these examples are provided only by way of illustrations of the object of the invention and do not constitute a limitation in any way.

EXAMPLE 1

Peeling with a Composition Based on *Rosa canina* Fruits

*Rosa canina* fruits are reduced into very fine powder in a cutting mill, then the powder that is obtained is passed successively into two sieves, the first of 500 μm and the second of 200 μm. The sieving product is added at a 2% level (p/p) to a mixture that comprises, in equal parts by weight, kernel oil of various Prunus, hydrogenated palm oil and *Euphorbia seifera* wax, then the whole mixture is homogenized.

On a face whose skin was previously cleaned, 1 g of the thus prepared composition is deposited on the forehead and on the cheeks, and it is massaged uniformly for about 5 minutes. The face is then cleaned very carefully with a cleaning solution or a mild and non-alkaline soap such as those conventionally used for face care.

EXAMPLE 2

Peeling with a Composition Based on Powder of *Cercis australis* Wood

*Cercis australis* wood is reduced into very fine powder in a cutting mill, then the powder that is obtained is passed through a 200 μm sieve. The sieving product is suspended in a mixture of water and glycerol (50/50, v/v) at a rate of 10 g of product per 20 ml of purified water/glycerol mixture, and the whole mixture is homogenized.

On a face whose skin was previously cleaned, 1 g of this suspension is deposited on the forehead and on the cheeks, and it is massaged uniformly for about 5 minutes. Then, excess suspension is eliminated by means of a wet cloth.

EXAMPLE 3

Peeling with a Composition Based on Powder of *Ficus carica* Leaves

By following an operating procedure that is identical to the one that is described in Example 1, a homogeneous suspension that contains 10 g of powder of dry *Ficus carica* leaves is prepared in 20 ml of a mixture of purified water/glycerol (50/50, v/v).

1 g of this suspension is applied to the forehead and the cheeks of a face whose skin was previously cleaned, and it is massaged uniformly for about 5 minutes. Then, excess suspension is eliminated by means of a wet cloth.

EXAMPLE 4

Peeling with Entire Leaves of *Ficus carica*

Dry *Ficus carica* leaves are rehydrated by soaking in a mixture of purified water and glycerol (50/50, v/v). Once these leaves are totally rehydrated, they are applied to the forehead and the cheeks of a face whose skin was previously cleaned, and it is rubbed gently for about 2 minutes.

EXAMPLE 5

Peeling with a Composition Based on Fresh Pulp of the Yucca Species

Fresh leaves or fresh stems of the Yucca species are ground by means of a cutting mill, then an equal weight of purified water is added to the ground material that is obtained. The resulting suspension is passed into a 100 μm sieve, then it is homogenized.

On a face whose skin was previously cleaned, 1 g of this suspension is deposited on the forehead and on the cheeks, and it is massaged uniformly for about 5 minutes. Then, excess suspension is eliminated by means of a wet cloth.

In all of the cases described above, a slight redness of the face appeared immediately following the massage. This redness gradually increased, while being accompanied most often by a slight sensation of heat, then disappeared at the end of several hours. A very uniform exfoliation of the treated skin areas was observed about 2 to 3 days after the massage was carried out. The regeneration of the epidermal cells following this exfoliation is reflected by an improvement in the constitution of the tint, a reduction of the skin pore size and a smoothing of the surface of the skin.

What is claimed is:

1. A method of superficially peeling epidermal tissue comprising the steps of introducing into the horny layer of the skin of a human being an element comprising hair of vegetable origin selected from the hair of the fruit of *Rosa canina,* said hair having a rigidity, size and shape sufficient to cleave and penetrate said horny layer and having a length of about 5 to about 100 millimicrons.

2. The method of claim 1 further massaging said hair into the horny layer for from about 2 to about 10 minutes sufficient to cause cleavage and penetration.

3. The method of claim 2, further cleaning and rinsing the massaged areas and then applying a cosmetic composition thereto high in fatty substances.

4. A dermatological method for superficial epidermal peeling comprising introducing into the horny layer of the skin of a human being, an element comprising hair of vegetable origin from the hair of the fruit of *Rosa canina,* said hair having a rigidity and shape sufficient to penetrate said horny layer and having a length of about 5 to about 100 microns.

5. The element of claim 4 wherein the element is present in an amount of from about 10% to about 40% by weight of a dermatologic preparation.

6. The method of claim 4 wherein the element comprises hair of fruit of *rosa canina* of a length of from about 20 to about 100 millimicrons.

* * * * *